United States Patent [19]
Fischel et al.

[11] 4,155,852
[45] May 22, 1979

[54] LOW LEAKAGE CURRENT MEDICAL INSTRUMENT

[75] Inventors: Halbert Fischel, 14802 Newport Ave., Apt. 2D, Tustin, Calif. 92680; Robert L. Anderson, Boulder, Colo.

[73] Assignee: Halbert Fischel, Los Angeles, Calif.

[21] Appl. No.: 743,223

[22] Filed: Nov. 19, 1976

[51] Int. Cl.² ........................................... B01D 31/00
[52] U.S. Cl. ................................... 210/186; 128/908; 210/321 B
[58] Field of Search ............... 210/186, 96 M, 321 B; 29/611; 361/43, 50, 49; 128/2.1 P

[56] References Cited
U.S. PATENT DOCUMENTS

| | | | |
|---|---|---|---|
| 3,352,779 | 11/1967 | Austin et al. | 210/96 M X |
| 3,513,540 | 5/1970 | Boggs | 29/611 |
| 3,573,551 | 4/1971 | Sircom | 361/43 |
| 3,670,206 | 6/1972 | Sircom | 361/50 |
| 3,722,680 | 3/1973 | Smith | 210/186 X |
| 3,757,169 | 9/1973 | Beresnikow | 361/49 |
| 3,946,738 | 3/1976 | Hewton et al. | 361/43 |

*Primary Examiner*—Frank A. Spear, Jr.
*Attorney, Agent, or Firm*—Fraser and Bogucki

[57] ABSTRACT

A medical instrument, specifically shown as a dialysis machine, incorporates an electrically isolated and hermetically sealed high thermal flux heater in conjunction with means for vectorially cancelling alternating current signal components generated in the operation of the machine. Because of electrical coupling between the medical instrument and a human patient blood stream, large ground leakage currents can result in electrical shock for a patient if the ground wire of the machine becomes open circuited. However, the combination of a specially modified dialysate fluid heater with an extremely large and dependable isolation resistance and operating mode dependent vectorial compensation for resistive and capacitive leakage current permits total leakage current from chassis to ground to be brought below a hitherto unattainable 1 microamp level.

11 Claims, 5 Drawing Figures

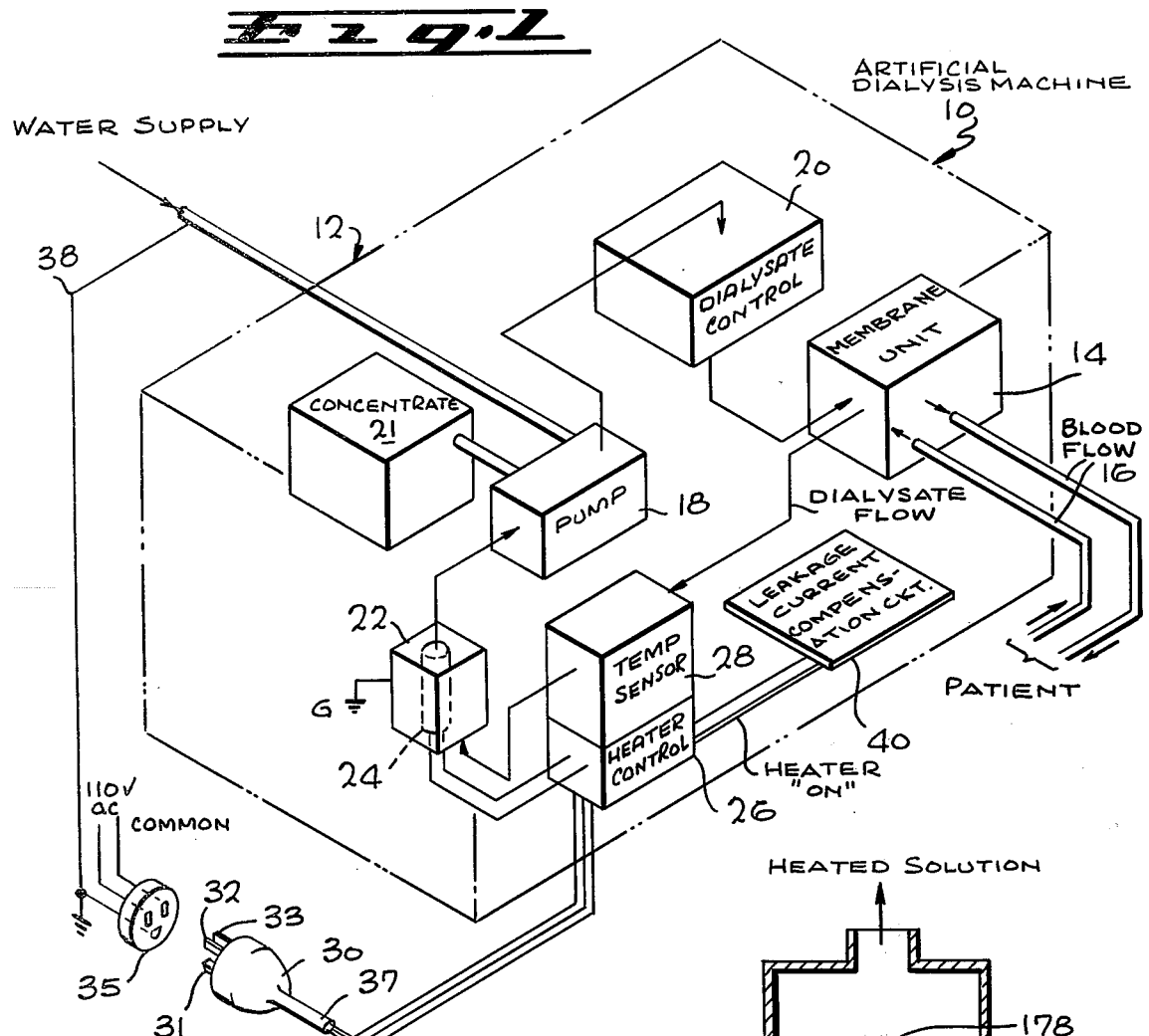
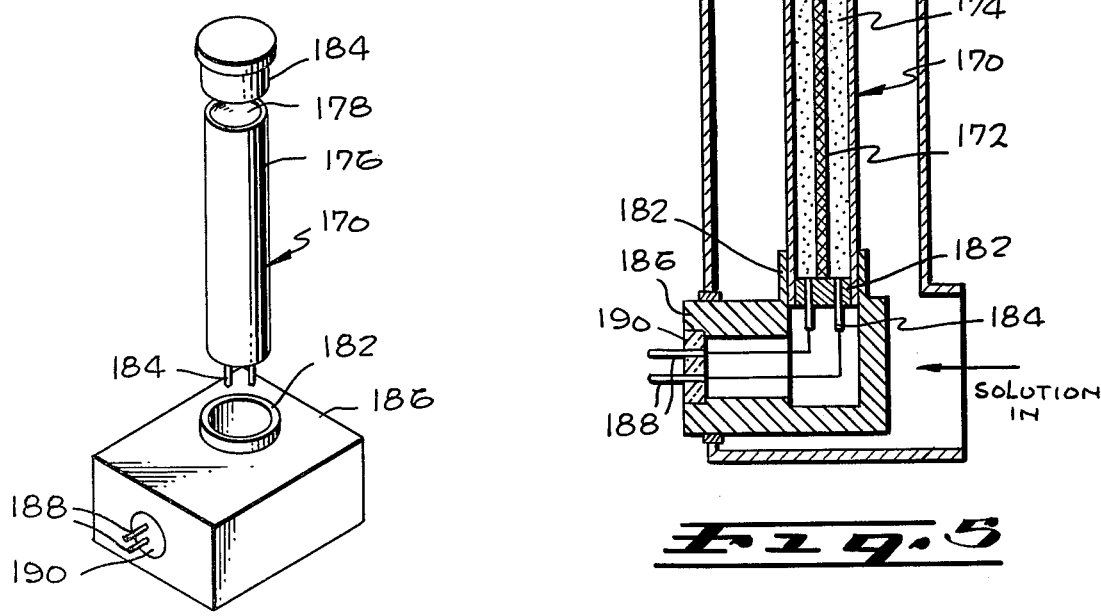

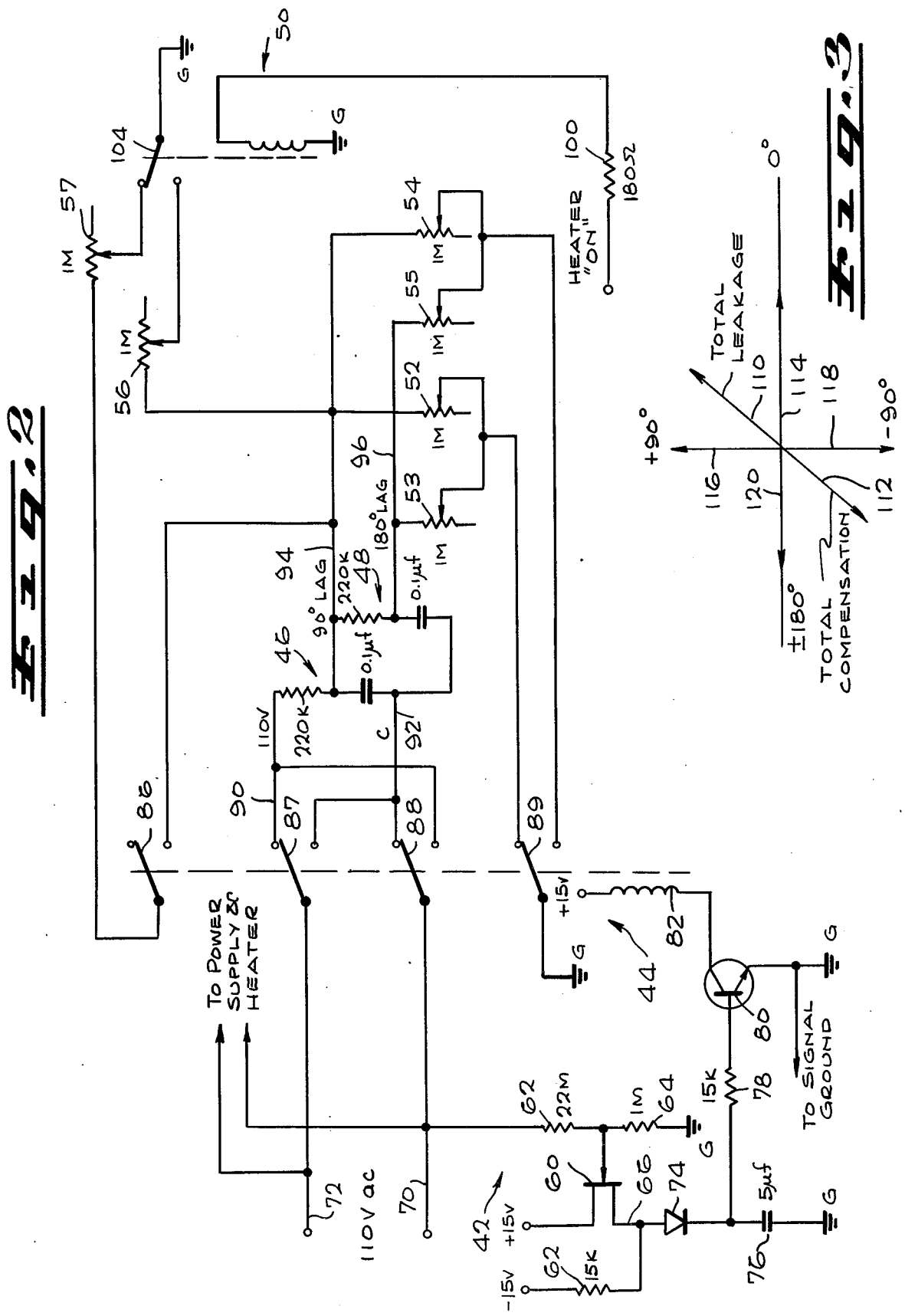

LOW LEAKAGE CURRENT MEDICAL INSTRUMENT

BACKGROUND OF THE INVENTION

With increasing refinements in and development of medical instruments which are capable of performing substitutive biological functions, increasing attention is being paid to potential hazards and side effects in the use of such instruments. One particularly significant hazard with medical instruments which are directly interconnected to patient tissue, such as the blood stream, is leakage current between the instrument chassis and ground. With an artificial dialysis machine, for example, the patient connected leads create circuits directly into the blood stream and the presence of excessive leakage current is unduly likely to affect the heart of the patient if directed through the patient. While such systems may or may not utilize electrical energy for pumping power, they are required to heat delivered dialysate solution and maintain control of its temperature, and this is conveniently done by electrical means in practical systems. Furthermore, the thermal energy required for heating is substantial, and the heater element is disposed for this reason in the dialysate solution flow path, so the heater element effectively is electrically coupled through the conductive dialysate solution and interchange membrane to the blood stream itself. With conventional 50 or 60 Hz alternating current excitation of the electrical circuits, it can be seen that leakage current can arise from ohmic coupling, which provides a component that is in phase with the exciting signal, and capacitive coupling which provide other components having a fixed phase relation to the exciting signal.

It is wholly inadequate under these circumstances to assume that adequate grounding of the chassis will provide the necessary degree of safety for the system and the patient. The grounding connection may become damaged or broken, either at the machine or otherwise, and the desired maximum of leakage current should not be exceeded under any conditions of possible energization of the circuitry. Thus, regardless of the manner in which the prongs of the connector plug for the power line are inserted into the socket, the leakage current should remain below the desired maximum level. Further, experience has shown with observation of many dialysis machines that the ohmic coupling component is highly variable between different machines, and variable with time and operating conditions even for a specific machine. Workers in the art have heretofore had substantial difficulty in decreasing total leakage current levels to less than 100 microamps.

SUMMARY OF THE INVENTION

Medical instruments in accordance with the invention utilize a high heat flux thermal energy source with a conductive solution, but the source is so arranged that ohmic coupling from the electrical heater element of the source to the conductive solution is minimal. Concurrently, capacitive coupling components are vectorially compensated for different modes of excitation by sensing and signal generating circuits which, together with the ohmic isolation, internally balance the current components within the system.

In a more specific example of a dialysis machine in accordance with the invention, a high heat flux resistive heating structure within the dialysate solution comprises the resistive heating element itself encompassed by an outer casing and insulated from the casing by a normally non-conductive powder or porous ceramic. The cylindrical housing for the heater has a welded sealed cap at one end and a hermetically sealed base at the other, but if the seals are not vacuum tight to about $10^{-9}$ Torr-liters per second they will not be adequate in practice to insure that minute amounts of water do not migrate into the interior of the element. Even minute amounts of water are sufficient to increase the conductivity of the heater dielectric, which is typically $Mg_2O_3$ powder, to provide an ohmic coupling path from the electrical heating element to the housing. Thus, in accordance with the invention, each end of the housng is hermetically sealed with a helium leakproof seal comprising an overlying cap structure at the one end and a receptacle including electrical connector means providing a physical extension of the male prongs issuing from the base of the housing, with both sealing elements being brazed to the housing structure after the insulative powder within the heater has been baked sufficiently to increase the internal heater resistance to an excess of 100 megohms.

To internally compensate the inductive and capacitive coupling components of ground leakage current within the dialysis machine, different conditions are taken into account to utilize RC networks to conduct currents of compensating phase and amplitude to ground. Current sensing means are also employed to switch between different RC networks, to introduce different and appropriate amounts of compensation dependent upon the manner in which the lines are excited. Automatically controlled compensation is also used for different conditions existing when the heater is on as opposed to when it is off. Small ground currents having phase of 90° and 180° lag relative to the AC input voltage are generated with precisely set compensating values so as to maintain total chassis to ground leakage current below 2 microampere.

BRIEF DESCRIPTION OF THE DRAWINGS

A better understanding of the invention may be had by reference to the following description, taken in conjunction with the accompanying drawings, in which:

FIG. 1 is a combined schematic representation of the principal elements of an artificial dialysis machine and block diagram of leakage current compensating circuits in accordance with the invention;

FIG. 2 is a schematic representation of circuits employed in the arrangement of FIG. 1;

FIG. 3 is a diagram illustrating phase relationships of leakage and compensation currents for the machine shown in FIG. 1;

FIG. 4 is a perspective view, partially broken away and partially exploded, of a heater element utilized in systems in accordance with the invention; and FIG. 5 is a cross-sectional view of the heater element of FIG. 4.

DETAILED DESCRIPTION

An artificial dialysis machine 10 is depicted only generally in FIG. 1 in order to provide a context for the circuits of the invention. The housing or chassis 12 for the machine contains a dialyzer membrane unit 14, which may be of the coil or plate type, in which passes the dialysate solution in interchange relationship with blood flowing in conduits 16 from the patient. The dialysate flow path also is depicted only generally, and includes a positive or negative pressure pump 18 used in circuit with a dialysate control 20, which may be a proportioning system mixing water from a utility water supply with concentrate from a container 21 or a central delivery system to the dialyzer membrane unit 14. Whether a closed or open loop system is used in the present instance is immaterial to the problem of minimization of leakage currents. In either event, dialysate flow passes through a heating chamber 22 within which a heater element 24 is disposed. The heater element 24 is turned on and off intermittently under normal operation by a heater control 26 which is responsive to a temperature sensor 28 in the dialysate flow path. It will be understood that the dialysis machine 10 of FIG. 1 is merely a very general example of a medical instrument, and that the problems presented by a heater 24 having a high thermal flux and disposed in the path of a conductive solution can have counterparts in other medical instruments.

The specific way in which the heater is constructed and arranged is described in greater detail in conjunction with FIGS. 3 and 4. However, in accordance with the invention the internal resistance between the electrical element and outer case of the heater 24 is established and maintained in excess of approximately 100 megohms even though the heater element of less than 3" in length and 1" in diameter outputs up to 2400 watts. When this condition is established and maintained in accordance with the teachings of the present invention, ohmic coupling of the heater 24 to internal ground (designated "G" in the figures) is negligible, and less than 1 microampere. The chassis 12 of the machine 10 is electrically connected to internal ground.

Electrical energy for the dialysis machine is a normal household and institutional 110 volt, 60 Hz supply, (which may be at 50 Hz or other voltage levels in accordance with available power sources) although the ordinary U.S. and Canadian context will be described herein. Thus a three prong connector plug 30 having a ground connection 31 and a pair of prongs 32, 33 is plugged into a conventional socket 35, with a first prong 32 normally being coupled to a common line and the second prong 33 being in circuit with the 110 volt AC line. However, it cannot be assumed that the ground connection will maintain its integrity, either in the power line 37 to which the plug 30 is connected, or in the external ground circuits, and the prongs 32, 33 may be inserted in a normal position or in a reverse position, as for example if someone were to improperly utilize a three pin to two pin adapter or if the outlet is improperly connected. Thus modern safety standards require that leakage currents be acceptably low from the chassis 12 to ground, whatever mode of operation or plug insertion is employed. In addition, a short circuit electrical connection 38 is made between the electrical utility ground which connects to terminal 31 and all other ground connections of machine 10 such as the utility water supply. This avoids any problem of current being conducted through machine 10 because of slightly different ground potentials existing at different ground connection points.

To this end, a leakage current compensation circuit 40 is incorporated within the machine 10 and is coupled to provide compensating currents to the internal or chassis ground of the machine 10. The current compensation that is required depends primarily upon whether the electrical plug 30 is connected with normal or reversed polarity and whether or not the heater 22 is operating. The commpensation circuit 40 is thus controlled in accordance with one of four possible operating modes dependent upon these conditions to provide preselected ground currents to compensate for and cancel ground leakage current. The four modes are listed below in Table I.

Table I

Mode 1—normal polarity and heater off.
Mode 2—normal polarity and heater on.
Mode 3—reverse polarity and heater off.
Mode 4—reverse polarity and heater on.

Referring now to FIG. 2, the leakage current compensation circuit 40 is shown as including a polarity detector circuit 42, a four-pole relay 44 that is controlled by polarity detector circuit 42, 90° phase lag generating circuits 46, 48, a heater on relay 50 which responds to the heater on signal from heater control 26, and a plurality of 1 megohm adjustable resistances 52–57.

The plug polarity detector 42 includes an FET transistor 60 coupled in series with a 15 K resistor 62 between +15 volts and −15 volts. The gate of transistor 60 is coupled to the common point of large voltage divider resistances 62, 64 and therefore the voltage at the source 66 of transistor 60 closely follows the voltage at the common point of voltage divider resistor 62, 64. Therefore, if the plug 30 is connected with the proper polarity, conductor 70 is connected to common and remains substantially at ground potential. On the other hand, if the plug polarity is reversed with conductor 72 being connected to common, a 110 volt AC voltage appears on conductor 70 which is divided by resistors 62 and 64 to produce approximately 4.8 volts AC at source 66.

The source 66 is couupled through a half wave rectifying diode 74 to a storage capacitor 76 which becomes charged to approximately +4 volts when terminal 70 is connected to 110 volts AC and remains at substantially ground potential when termainal 70 is connected to common. The stored voltage at the junction of diode 74 and capacitor 76 is coupled through a 15 K resistor 78 to the base of an NPN transistor 80. The collector of transistor 80 is coupled through an actuation coil 82 of relay 44 to +15 volts and the emitter of transistor 80 is connected to chassis ground. As indicated, the chassis ground is connected to signal ground provided by the output of the power supply and is thus constrained to remain at substantially a potential midway between the peak voltage excursions of the 110 volt AC power signal regardless of the polarity of connection of plug 30. Thus, if the plug 30 is properly connected, the voltage across capacitor 76 is zero, transistor 80 is in an off state, and relay 44 is deenergized as shown. However, in the event that the plug connection is reversed, the AC signal occuring at source 66 is rectified to turn on transistor 80 and thereby energize relay coil 82 to switch relay 44 to a state opposite that which is shown in FIG. 2.

Relay 44 has four poles 86–89 which are selectively switched in response to the energization of coil 82. Poles 87 and 88 are coupled to power line conductor 72, 70 respectively and their two pairs of contacts are connected such that a conductor 90 always carries 110 volts AC and a conductor 92 is always connected to electrical power common.

An RC 90° phase lag circuit 46 is coupled between conductors 90 and 92 to provide a voltage signal on a conductor 94 which lags the AC power supply voltage signal by approximately 90°. A second RC 90° phase lag circuit 48 is coupled between 90° lag conductor 94 and common conductor 92 to provide a voltage signal on a conductor 96 with an additional approximate 90° of phase lag relative to the 90° lag signal or a total of approximately 180° lag relative to the AC power supply voltage.

The 90° lag voltage signal appearing on conductor 94 is connected to variable resistances 52 and 54 while the 180° lag voltage signal appearing on conductor 96 is connected to variable resistances 53 and 55. The variable resistances 52 and 53 are then coupled through the wiper arms thereof to the deenergized contact of relay 44 corresponding to wiper arm 89. Wiper arm 89 is connected to chassis ground. Thus, when the machine 10 is connected with plug 30 in the proper orientation with the heater 22 turned off, the variable resistances 52 and 53 can be adjusted to compensate ground leakage current until the total compensated ground current is less than 2 microamps. This ground leakage current in mode 1 where the plug is properly connected and the heater is off is due largely to capacitive coupling between the power supply and chassis and between pump drivers and the chassis and remains extremely constant. It thus becomes possible to preset the resistances 52 and 53 and maintain excellent compensation between intervals of scheduled major maintenance activities.

Similarly, if the plug 30 is connected with a reverse polarity, the required compensation currents may also be predicted, though they will typically be different from the currents required when connected with the proper polarity. If plug 30 is connected with the reverse polarity, this is sensed by the polarity sensing circuit 42 which energizes relay 44 and causes the movable wiper arms of resistances 54 and 55 to be connected through contact arm 89 to ground. Resistances 54 and 55 may thus be adjusted to provide compensation for ground leakage current with the plug connection reversed and the heater off.

Relay 50 is shown in a deenergized or heater off state. However, in the event that the heater on command signal appears, current flows through 180 ohm resistor 100 and relay coil 102 to energize relay 50 and move the contact arm 104 to the position opposite that in which it is shown in FIG. 2. When the heater is off, the electrical heating element is maintained at common or ground potential and there is no capacitive coupling between the electrical heating element 24 and the chassis 12. Thus, even though resistances 57 is coupled between relay 50 and the contact arm 86 of relay 44, no heater compensation is provided in mode 1 when the plug 30 is connected with a normal polarity and the heater is off. However, in the event that the plug 30 is connected with reverse polarity, 110 volts AC is applied to the electrical heating element 24 even when the heater is off and capacitive coupling thus exists between the electrical heating element 24 and chassis ground. Under this circumstance, relay 44 is energized to connect contact arm 86 to 90° lag conductor 94 and cause a 90° lag current to flow through variable resistance 57. Since the capacitively coupled ground leakage current through the heater 22 has a 90° lead phase relationship to the power supply voltage, the compensating current through resistance 57 can be adjusted to exactly cancel this leakage current.

In modes 2 and 4 when the heater 24 is on, a substantially identical capacitive coupling exists between the electrical heating element 24 and the chassis 12. Therefore, relay 50 is coupled to be actuated under either condition of plug polarity when the heater is on to couple the 90° phase lag voltage on conductor 94 to ground through variable resistance 56 and wiper arm 104. After resistances 52 and 53 or 54 and 55 have been adjusted for proper current magnitudes with corresponding plug polarity connections with the heater off, the heater can be turned on and resistance 56 adjusted to compensate for the additional capacitive coupled ground leakage current caused by the energization of the heater 24. Because of the special construction of the heater as described below, resistive coupling between the electrical heating element 24 and the chassis 24 remains so small throughout the life of the machine 10 that no compensation for resistive leakage currents through the heater is necessary.

Referring now to FIG. 3, there is shown a phase diagram illustrating the total leakage current 110 and the total compensation current 112 which is equal in magnitude and opposite in phase to the total leakage current 110. The total leakage current 110 is comprised of a resistive component 114 which is in phase with the power supply AC voltage and a capacitive reactive component 116 which has a phase angle of +90° relative to the AC power supply voltage. As explained previously, the resistances 52, 54, and 56 are adjusted to provide a magnitude of 90° phase lag compensating current 118 in response to the 90° phase lag voltage appearing on conductor 94 which exactly compensates the 90° phase leakage current 116 for any given mode of operation. Similarly, for any given mode of operation, the resistances 53 and 55 are adjusted to provide a proper magnitude of 180° phase lag compensating current 110 in response to the 180° phase lag voltage appearing on conductor 96 to compensate the resistive component of the leakage current 114. Thus, for any given mode of operation, the total compensation current 112 may be adjusted to substantially cancel the total leakage current 110 and the resultant ground leakage current of the machine 10 may be maintained at less than 2 microamps.

Referring now to FIGS. 4 and 5, a high thermal flux heating element 170 basically comprises a central column 172 of resistive material, and may advantageously utilize a double helix winding as taught in U.S. Pat. No. 2,831,951, surrounded by $Mg_2O_3$ insulative powder 174 within a cylindrical outer case 176. The cylindrical case is typically of Incoloy 800, and one end is closed by an end cap 178 which is welded about its periphery to the inside edge of the case 176. Although high quality standards may be observed with the welding, in practical usage, probably due to the high thermal stresses imposed when the heater 170 is operating, the weldments are not moisture proof. Consequently, the $Mg_2O_3$ insulation 174, which has extremely high resistivity when dry, drops remarkably in resistive value, due to the substantial capacity of the powder for taking up moisture. The opposite end of the heater 170 includes a lava plug 182 through which a pair of male prongs 184 extend for external circuit connection, there being supposedly a seal between the lava plug 182, the male connectors 184 and the inner wall of the housing 176. Again, a true moisture proof seal is not achieved by this construction alone.

In accordance with the invention, therefore, unique methods are utilized to provide a virtually zero current leakage heater. First, the heater is baked at a temperature in the range of 550° F. for approximately ten hours in this example. With the Mg$_2$O$_3$ layer 174 baked to a dryness such that the resistance between terminals 184 and case 176 is greater than 100 megohms, satisfactory operation can be obtained, and with careful procedures it has been found feasible to provide values in excess of 1×10$^9$ ohms.

Immediately upon baking, an end cap 184 of stainless steel is silver brazed over the end piece 178 and the associated terminal portion of the housing 176. This procedure is carried out at 1100° F., and the seal may be promptly checked with helium leakage detection equipment to insure that it has a vacuum integrity of at least 10$^{-9}$ Torr-liters per second. If this vacuum integrity requirement is not met, the end cap 184 must be replaced and resealed. The base portion of the heater 170 is then inserted into a stainless steel body 186 with the prongs 184 in electrical circuit with male connectors 188 mounted in a glass insulator 190 and hermetically sealed to the stainless body and to the prongs 188 by a glass-to-metal seal. The lower portion of the heater 170 is received within a collar 182, to which it is internally silver brazed, again at 1100° F. This seal may again be progressively checked to determine whether it meets the vacuum integrity requirement of at least 10$^{-9}$ Torr-liters per second.

The resultant structure takes up only very little more space than the principal heater element itself, and can be mounted in a chamber 22 through which the dialysate solution passes. The heat output of the heater element is not affected, but leakage currents are kept at acceptably minute levels through the useful life of the heater.

While a number of alternatives and modifications have been described above, it will be appreciated that the invention is not limited thereto but encompasses all improvements and modifications in accordance with the scope of the appended claims.

What is claimed is:

1. A medical machine having different known ground leakage currents in each of a plurality of different modes of operation, the machine comprising at least one machine element that is electrically coupled to human tissue and a ground leakage current compensation circuit including means generating different compensation currents to ground, each with a predetermined magnitude and phase relationship to compensate the known ground leakage current associated therewith in the given mode of operation, wherein the compensation circuit further includes a plug polarity detector providing an actuation signal indicative of a polarity with which the machine is electrically connected to an AC power source having a common terminal and a power terminal carrying an AC voltage and a switching network responsive to the actuation signal and coupling given common and AC voltage conductors of the compensation circuit to the common and AC voltage terminals respectively of the AC power source regardless of the polarity of a plug connection made thereto.

2. The medical machine according to claim 1 above, wherein the plug polarity detector includes circuitry coupled to detect a difference between a voltage potential appearing on a conductor connected to one of the AC power source terminals and ground potential and wherein the ground potential is approximately half way between maximum positive and negative excursions of the voltage on the AC power power terminal of the power source.

3. The medical machine according to claim 1 above, wherein the compensation circuit further includes a phase shift circuit coupled between the common and AC voltage terminals of the compensation circuit and providing as an output a voltage signal with a phase shifted relative to the phase of the voltage on the AC voltage terminal, and a variable resistance coupled between the output of the phase shift circuit and ground.

4. The medical machine according to claim 3 above, further comprising a second variable resistance and means responsive to an operating mode of the machine for selectively coupling a selected one of the first mentioned and second variable resistances to ground.

5. The medical machine according to claim 1 above, wherein the compensation circuit further includes a first phase shift circuit coupled between the common and AC voltage conductors of the compensation circuit to provide a first output voltage signal having a 90° lag phase relationship relative to the voltage signal on the AC voltage conductor and a second phase shift circuit coupled between the common terminal and the first output voltage signal to provide at a second output a voltage signal having a 90° lag phase relationship relative to the first output voltage signal.

6. The medical machine according to claim 5 above, wherein the compensation circuit further includes means coupled to provide a selected resistance between ground and the first output voltage signal and between ground and the second output voltage signal for each of a plurality of different operating modes of the machine, said resistances being selected to provide compensation currents which compensate ground leakage currents of the machine to reduce the compensated ground leakage current of the machine below 2×10$^{-6}$ ampere.

7. The medical machine according to claim 1 above, further comprising a heater electrically coupled to human tissue, the heater having an outer case, an electrical heating element and material insulating the electrical heating element from the outer case, the outer case having an hermetic seal which enables the insulating material to maintain a resistance greater than 100 megohms between the electrical heating element and the case notwithstanding submersion of the heater in water for long periods of time.

8. The medical machine according to claim 7 above, wherein the outer case includes separate portions which are bonded together by silver brazing to provide a helium leakproof seal greater than 10$^{-9}$ Torr-liters per second.

9. The medical machine according to claim 1 above, further comprising conductor means interconnecting all external ground connections of the machine, including an electrical ground connection and a water supply source to maintain said ground connections at the same voltage potential.

10. A kidney dialysis machine comprising:
   a membrane unit providing an exchange between human blood and a dialysate solution;
   a dialysate control system connected to circulate dialysate solution through the membrane unit;
   a heater having an electrical heating element and a case disposed in heat transfer relationship with the circulating dialysate solution, the heater maintaining a high electrical resistance greater than 100 megohms between the electrical heating element and the case; and
   a ground leakage current compensation circuit providing different compensation ground currents of phases and magnitudes which compensate ground leakage currents of the kidney dialysis machine for each of different operating modes dependent upon energization and nonenergization of the heater to reduce the compensated ground leakage curent of the machine below $2 \times 10^{-6}$ ampere.

11. The kidney dialysis machine according to claim 10 above, wherein said different operating modes further depend upon the relative polarity with which the machine is electrically connected to an AC electrical power source.

* * * * *